United States Patent
Okamura et al.

(10) Patent No.: US 7,104,687 B2
(45) Date of Patent: Sep. 12, 2006

(54) X-RAY DIAGNOSIS APPARATUS HAVING A COMMON COOLER

(75) Inventors: Hidefumi Okamura, Chiba (JP); Motomichi Doi, Ibaraki (JP)

(73) Assignee: Hitachi Medical Corporation, Tokyo (JP)

( * ) Notice: Subject to any disclaimer, the term of this patent is extended or adjusted under 35 U.S.C. 154(b) by 155 days.

(21) Appl. No.: 10/479,998

(22) PCT Filed: Jun. 7, 2002

(86) PCT No.: PCT/JP02/05665

§ 371 (c)(1), (2), (4) Date: Jun. 9, 2004

(87) PCT Pub. No.: WO03/002001

PCT Pub. Date: Jan. 9, 2003

(65) Prior Publication Data

US 2004/0234040 A1    Nov. 25, 2004

(30) Foreign Application Priority Data

Jun. 7, 2001   (JP) .............................. 2001-172543

(51) Int. Cl.
*H01J 35/10*   (2006.01)
*H01J 31/49*   (2006.01)
*G01T 1/24*    (2006.01)

(52) U.S. Cl. ...................... 378/200; 378/141; 378/189; 378/199; 250/370.15

(58) Field of Classification Search .................. 378/19, 378/98.8, 141, 142, 189, 190, 193, 196–200; 250/370.09, 370.15
See application file for complete search history.

(56) References Cited

U.S. PATENT DOCUMENTS

| | | | | |
|---|---|---|---|---|
| 4,456,826 A | * | 6/1984 | Forster | 250/370.09 |
| 4,651,338 A | * | 3/1987 | Hahn | 378/199 |
| 4,709,559 A | * | 12/1987 | Dotzauer et al. | 62/499 |
| 4,831,639 A | * | 5/1989 | Harke | 378/19 |
| 4,969,167 A | * | 11/1990 | Zupancic et al. | 378/19 |
| 5,552,608 A | * | 9/1996 | Gallagher et al. | 250/370.15 |
| 5,610,968 A | * | 3/1997 | Deucher et al. | 378/199 |
| 5,761,269 A | * | 6/1998 | Sugihara et al. | 378/199 |
| 5,912,943 A | * | 6/1999 | Deucher et al. | 378/98.8 |
| 6,370,881 B1 | * | 4/2002 | Maydanich | 62/3.2 |
| 6,411,672 B1 | * | 6/2002 | Sasaki et al. | 378/19 |
| 6,412,979 B1 | * | 7/2002 | Hell et al. | 378/200 |
| 6,511,224 B1 | * | 1/2003 | Lu et al. | 378/199 |
| 6,519,317 B1 | * | 2/2003 | Richardson et al. | 378/130 |
| 6,669,366 B1 | * | 12/2003 | Busse et al. | 378/199 |
| 6,709,156 B1 | * | 3/2004 | Hell et al. | 378/199 |

\* cited by examiner

*Primary Examiner*—Allen C. Ho
(74) *Attorney, Agent, or Firm*—Antonelli, Terry, Stout and Kraus, LLP.

(57) ABSTRACT

An X-ray diagnosis apparatus is disclosed which includes two different cooling circuits and a single cooling portion. A first heat transfer medium is circulated for absorbing heat generated in the X-ray generator. A second heat transfer medium is circulated for absorbing the heat generated in the planer type X-ray detector. A heat exchanger is provided for exchanging heat between the first heat transfer medium and the second heat transfer medium. The cooling portion is coupled to the cooling circuit carrying the second heat transfer medium in order to cool the second heat transfer medium.

12 Claims, 3 Drawing Sheets

X-RAY DIAGNOSIS APPARATUS HAVING A COMMON COOLER

TECHNICAL FIELD

The present invention relates to an X-ray diagnosis apparatus or an X-ray examination apparatus (hereinafter, generically referred to as "X-ray diagnosis apparatus"), and more particularly, to a technical field of cooling an X-ray generator for generating X-rays and a planer type X-ray detector for detecting X-rays.

BACKGROUND ART

An X-ray diagnosis apparatus is used for diagnosis and the like of an object by taking an X-ray photograph of the object by irradiating X-rays generated from an X-ray generator to the object and exposing a film with X-rays having passed through the object. Further, the X-ray diagnosis apparatus is also used for diagnosis and the like by detecting X-rays having passed though the object using a planer type X-ray detector composed of a plurality of X-ray detecting elements disposed two-dimensionally and flatly, and by drawing an X-ray image having a distribution of intensity and density of the detected X-rays on a monitor in place of a film.

Since the planer type X-ray detector used in the X-ray diagnosis apparatus and the like generates heat in operation, when the characteristics of detected X-rays are changed by a temperature change due to the generated heat, there is a possibility that the quality of the X-ray image is changed.

To cope with this problem, temperature change of the planer type X-ray detector is prevented by a cooler using a Peltier element as disclosed in, for example, Japanese Unexamined Patent Publication No. 11-271456. That is, the planer type X-ray detector including semiconductor materials such as gallium and arsenic etc. is hermetically sealed in a glass casing or the like so that it is not adversely affected by moisture and the like, the Peltier element is bonded on the glass casing, and a heat sink is attached to the radiating surface of the Peltier element. The heat sink is forcibly cooled by an air cooling fan as well as heat is radiated therefrom by convection, thereby the X-ray detector is cooled through the Peltier element and the glass casing.

On the other hand, as a cooler of the X-ray generator for generating X-rays, there is a circulation cooling system is employed as disclosed in, for example, Japanese Patent Application No. 11-367296. In the circulation cooling system, a vessel, in which an X-ray tube is accommodated, is filled with insulating oil as a heat transfer medium, the insulating oil is continuously extracted to the outside of the vessel and returned thereinto after it is cooled.

Although the heat generated by the planer type X-ray detector is about 0.1 kw, it is required to stably keep the X-ray detector within a predetermined temperature range (for example, from a room temperature to about 35° C.) to prevent deterioration of image quality. In contrast, when imaging is executed using a film, since the X-ray generator consumes power of about 20 to 30 kw for several seconds, it generates heat in a quantity large than that of the planer type X-ray detector. However, it is sufficient to keep the X-ray generator at a temperature equal to or less than 75° C. Further, although power consumption in fluoroscopy executed using the planer type X-ray detector is about 0.2 to 0.6 kw, power is consumed for a long time (for example, one hour).

As described above, since the planer type X-ray detector and the X-ray generator generate heat in a different quantity and are kept at a different temperature, they have coolers provided individually in the conventional art, and it is not taken into consideration to commonly use one of the coolers by both the devices.

DISCLOSURE OF INVENTION

An object of the present invention is to enable a cooler of an X-ray generator and a cooler of a planer type X-ray detector to be used commonly to thereby reduce the number of necessary coolers.

To achieve the above object, an X-ray diagnosis apparatus according to the present invention is comprising an X-ray generator for irradiating X-rays to an object, a planer type X-ray detector for detecting the X-rays having been irradiated from the X-ray generator and having passed through the object, a heat transfer medium for absorbing the heat generated in the X-ray generator and the heat generated in the planer type X-ray detector, a cooling means for cooling the heat transfer medium heated by absorbing the heat; and a means for moving the heat transfer medium between the X-ray generator, the planer type X-ray detector, and the cooling means.

That is, the heat transfer medium, which is conventionally recycled only to the X-ray generator, is also recycled to the planer type X-ray detector so that the heat of both the X-ray generator and the planer type X-ray detector is transferred by the heat transfer medium, and the heat transfer medium is cooled by the shared cooling means to thereby cool the X-ray generator and the X-ray detector.

In this case, the cooling means may be composed of a first cooling means for cooling the heat transfer medium flowing out from the X-ray generator and a second cooling means for cooling the heat transfer medium flowing out from the planer type X-ray detector, and the means for moving the heat transfer medium may be formed of a tubular member.

Further, the first cooling means may be composed of a heat exchanger in which heat is exchanged between the heat transfer medium flowing out from the X-ray generator and the heat transfer medium flowing out from the planer type X-ray detector.

When water whose specific heat is large is used as the heat transfer medium of the present invention, the cooling efficiency of the heat transfer medium is improved and the heat transfer medium can be easily handled.

Further, it is preferable that the means for moving the heat transfer medium between the planer type X-ray detector and the cooling means be composed of a control means for detecting the temperature of the heat transfer medium flowing into the planer type X-ray detector and controlling the cooling means so that the detected temperature is kept within a set range. According to this arrangement, the operating temperature of the X-ray detector can be kept constant.

Here, the X-ray detector of the present invention may be arranged such that provides a plurality of X-ray detecting elements disposed two-dimensionally and flatly are hermetically sealed in a casing and a cooling tube, into which the heat transfer medium flows, is thermally connected to one of the surfaces of the casing on which the X-ray detecting elements are disposed. This arrangement is preferable because the cooling efficiency can be improved by directly cooling the X-ray detector. Further, a heat conductive plate may be attached to one of the surfaces of the casing, in which the plurality of X-ray detecting elements disposed two-dimensionally and flatly are hermetically sealed, and the cooling tube, in which the heat transfer medium flows, may be thermally attached to the heat conductive plate. According to this arrangement, the cooling efficiency can be improved because a heat absorbing area through which heat is absorbed from the casing is increased. Further, a plurality of X-ray detecting elements may be accommodated in a casing one of the surfaces of which opens, the open surface of the casing may be hermetically sealed by the heat conductive plate and the cooling tube, in which the heat transfer medium flows, may be thermally attached to the outside surface of the heat conductive plate. In any of the cases, it is preferable that a copper tube be used as the cooling tube and that the cooling tube be attached to the surface in a meandering shape.

BEST MODE FOR CARRYING OUT THE INVENTION

Figure 1:
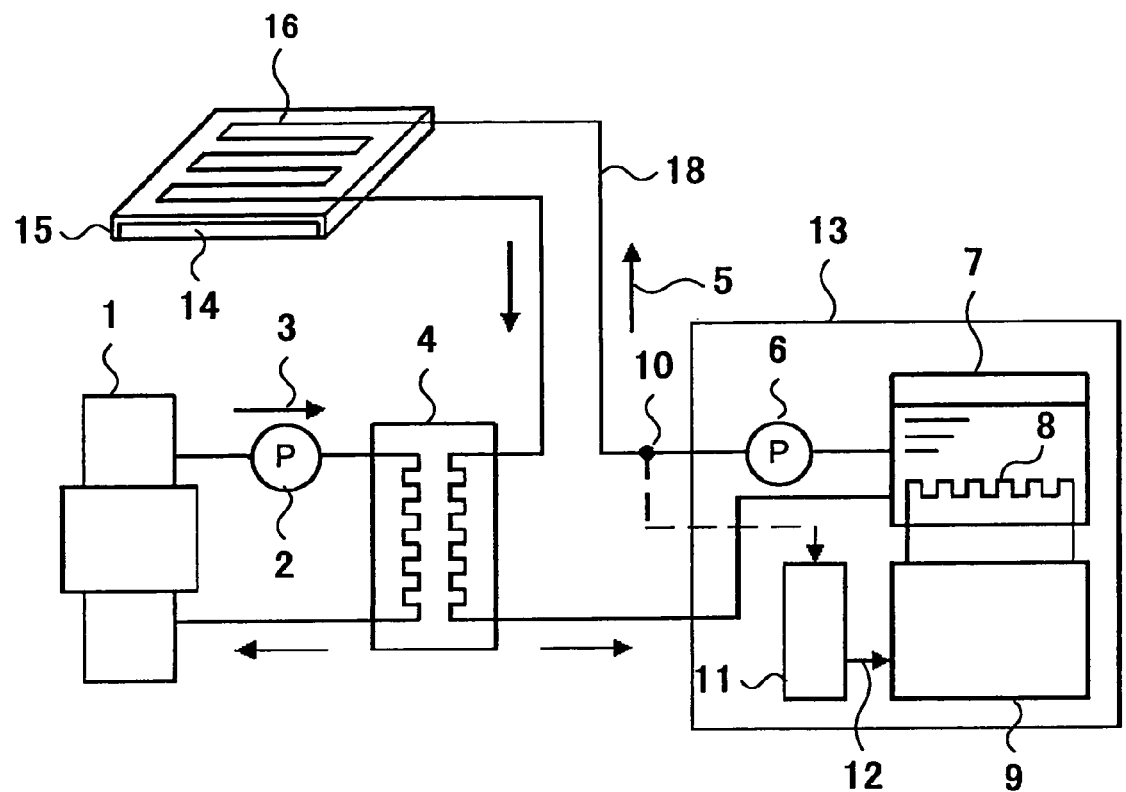
FIG. 1 is a system arrangement diagram of a cooling system that is a characteristic portion of an X-ray diagnosis apparatus according to an embodiment of the present invention.
Figure 2:
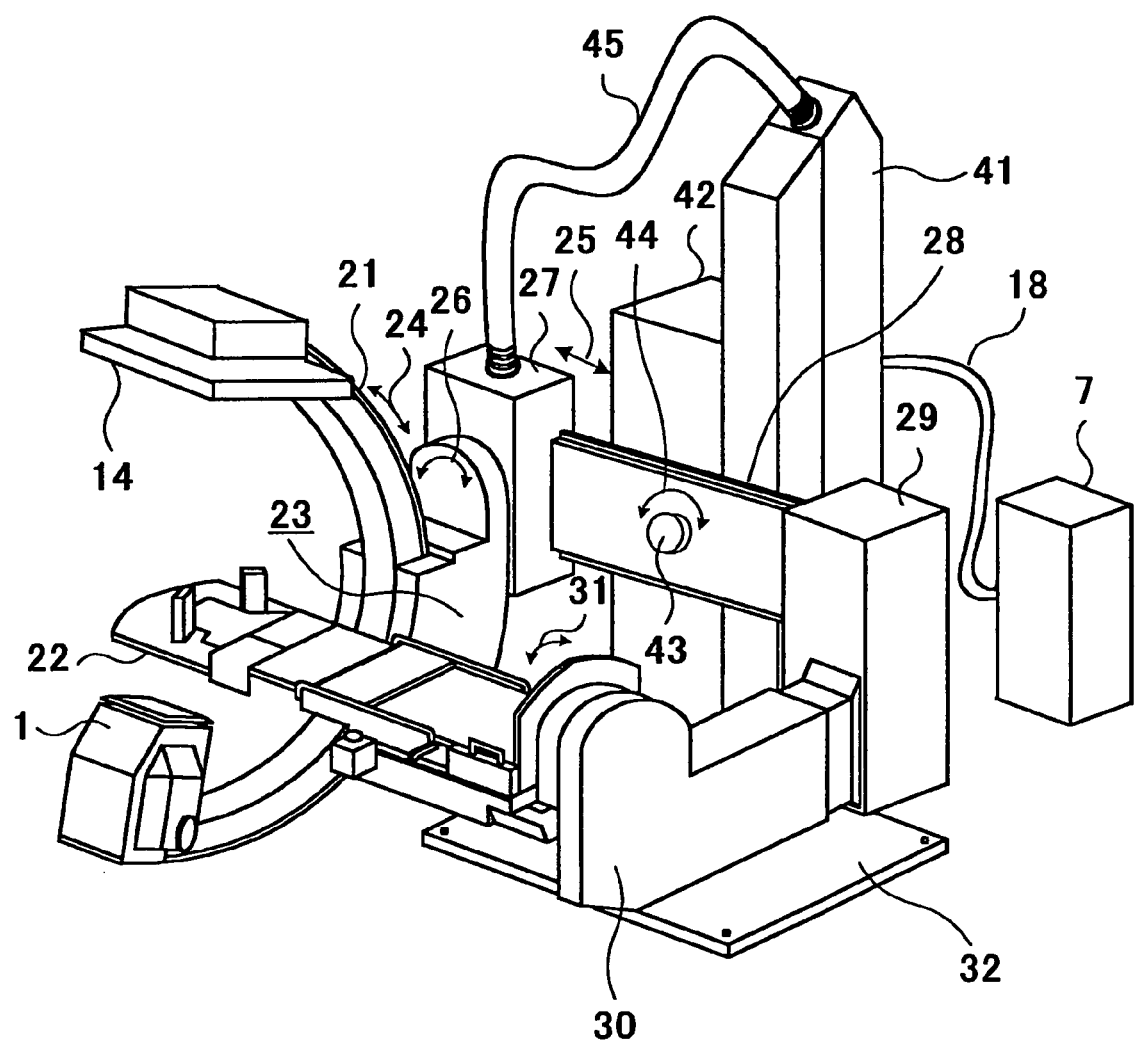
FIG. 2 is an outside view of the X-ray diagnosis apparatus of the embodiment to which a cooling system of FIG. 1 is applied.

An embodiment of the present invention will be explained below with reference to the accompanying drawings. FIG. 1 shows a system arrangement diagram of a cooling system that is a characteristic portion of an embodiment of the present invention, and FIG. 2 shows an outside view of an X-ray diagnosis apparatus of an embodiment to which the cooling system of FIG. 1 is applied.

As shown in FIG. 1, the cooling system of the embodiment of the present invention cools an X-ray tube device 1 and a planer type X-ray detector 14 by cooling water 5 acting as a heat transfer medium supplied from a single cooling device 13. The X-ray tube device 1 comprises an X-ray tube accommodated in a hermetically sealed vessel. Since a high voltage is applied to the X-ray tube of the X-ray tube device 1, high-voltage-resistant insulating oil 3 is used as the heat transfer medium. The X-ray tube device 1 is cooled by the insulating oil 3 circulating in the interior of the X-ray tube device 1. The insulating oil 3 is circulated by an oil pump 2 between the interior of the X-ray tube device 1 and a heat exchanger 4 for the X-ray tube device. The heat of the insulating oil 3 is exchanged with the heat of the cooling water 5 in the heat exchanger 4.

The X-ray detector 14 is accommodated in, for example, a glass casing 15, and a cooling tube 16, through which the cooling water 5 flows, is disposed on the upper surface of the glass casing 15. The cooling device 13 is provided with a cooling water tank 7 in which the cooling water 5 is stored, and the cooling water 5 in the cooling water tank 7 is suctioned by a cooling water pump 6 and introduced into a cooling tube 16 through a flexible resin cooling water tube 18. The cooling water 5, which has passed through the cooling tube 16, is introduced into the heat exchanger 4 through the cooling water tube 18, and the cooling water 5, which has passed through the heat exchanger 4, is returned into the cooling water tank 7 through the cooling water tube 18. In the cooling water tank 7, a liquefied refrigerant supplied from a refrigerator 9 is evaporated by an evaporator 8, thereby the cooling water 5 is cooled.

Further, a temperature measuring point 10 is disposed at a midpoint of the cooling water tube 18 through which the cooling water 5 is supplied to the cooling tube 16 for the X-ray detector 14 or on a discharge side of the cooling water pump 6 and detects the temperature of the cooling water 5 supplied to the cooling tube 16 for the X-ray detector 14. When the temperature of the cooling water 5 is lower than a set temperature (for example, a room temperature to 35° C.), the contact of a temperature relay 11 composed of a thermostat or the like opens, thereby a power supply input 12 to the refrigerator 9 is shut off. When the temperature of the cooling water 5 is higher than the set temperature, the contact of the temperature relay 11 closes, thereby the power supply input 12 is applied to the refrigerator 9. With this operation, the temperature of the cooling water 5 supplied to the cooling tube 16 is kept constant. Note that when the temperature of the cooling water 5 is controlled, the refrigerating capacity of the refrigerator 9 may be variably controlled or the circulating amount of the cooling water 5 may be controlled in place of turning on and off the operation of the refrigerator 9 by opening and closing the contact of the temperature relay 11.

The embodiment of the preferable X-ray diagnosis apparatus, to which the cooling system arranged as described above is applied, will be described with reference to FIG. 2. The X-ray tube device 1 and the planer type X-ray detector 14, which constitute the X-ray diagnosis apparatus, are secured to both the ends of a supporting arm 21 formed in an arc shape and disposed so as to confront each other across a bed 22 on which an object lies. The supporting arm 21 is supported by an arm supporting device 23 so as to slide in the direction of an arrow 24 shown in the figure, i.e., along the arc of the arm supporting device 23. The arm supporting device 23 is supported by a slider 27 so as to slide in the direction of an arrow 26 shown in the figure, thereby the arc surface of the supporting arm 21 is supported so that it tilts and turns. The slider 27 is supported by a beam 28 so as to slide in the longitudinal direction of the bed 22 (the direction of an arrow 25). A supporting column 29 is secured to an end of the beam 28. Further, a bed supporting member 30, which extends in a direction perpendicular to the beam 28, is disposed to the supporting arm 29, and the bed 22 described above is disposed at the extreme end of the bed supporting member 30 so as to incline in the direction of an arrow 31 shown in FIG. 2 about the axis of the bed 22 in a longitudinal direction. The beam 28 is rotatably supported by a supporting column 42 through a bearing 43 at approximately the center thereof in a longitudinal direction. A beam rotationally driving mechanism is disposed in the supporting column (not shown) of the bearing 43, and the beam 28 is turned in the direction of an arrow 44 by driving the beam rotationally driving mechanism. With this arrangement, the X-ray tube device 1, the X-ray detector 14, and the bed 22 can be tilted. Note that reference numeral 32 denotes a base of the X-ray diagnosis apparatus through which the apparatus is installed on a floor.

Further, although not shown, there are provided a high voltage generator and a controller used for the X-ray tube device 1, and a high voltage cable for connecting the high voltage generator to the X-ray tube device 1 is introduced thereto through a space formed in the interiors of a wiring pole 41, a wiring tube 45, the slider 27, the arm supporting device 23 and the supporting arm 21.

On the other hand, the cooling water tube 18, which is drawn out from the cooling device 7 that is the feature of the present invention is disposed to the cooling tube 16 of the X-ray detector 14 and to the heat exchanger 4 of the X-ray tube device 1 through the space formed in the interiors of the wiring pole 41, the wiring tube 45, the slider 27, the arm supporting device 23, and the supporting arm 21, similarly to the high voltage cable.

An operation of the X-ray diagnosis apparatus of the embodiment arranged as described above will be explained mainly as to an operation of the cooling system in a fluoroscopic mode. First, the cooling system is energized so that the cooling water 5 can be circulated between the cooling tube 16 of the X-ray detector 14 and the heat exchanger 4 of the X-ray tube device 1. Then, the position of a portion of the object to be subjected to fluoroscopy is determined by adjusting the direction and position of an axis connecting the X-ray tube device 1 to the X-ray detector 14 by actuating the motion of the arm supporting device 23 is in a state in which the object is laid on the bed 22. X-rays are generated by supplying a high voltage from the high voltage generator to the X-ray tube device 1, and X-rays, which have passed through the object, are detected by the X-ray detector 14. An X-ray fluoroscopic image is drawn on a monitor (not shown) based on a distribution of intensity of the detected X-rays on a two-dimensional plane.

In this fluoroscopic mode, the cooling water 5, which is discharged from the cooling water pump 6, flows into the cooling tube 16 of the X-ray detector 14 and cools the heat generated by the X-ray detector 14. Then, the cooling water 5, which flows out from the cooling tube 16, is subsequently introduced into the heat exchanger 4 of the X-ray tube device 1, cools the insulating oil 3 whose temperature has been increased by the heat generated by the X-ray tube device 1, and returns into the cooling water tank 7. The cooling water 5, which has returned into the cooling water tank 7, is cooled by the refrigerator 9. When the temperature of the cooling water 5, which has been suctioned from the cooling water tank 7 by the cooling water pump 6, is higher then the set temperature (for example, the room temperature up to 35° C.), the contact of the temperature relay 11 composed of the thermostat or the like is closed so that the power supply input 12 is supplied to the refrigerator 9. When the temperature of the cooling water 5 is lower than the set temperature, the contact of the temperature relay 11 is opened so that the power supply input 12 to the refrigerator 9 is shut off. The temperature of the X-ray detector 14 can be kept constant by controlling the temperature of the cooling water on the outlet side of the cooling water pump 6 as described above.

As described above, according to this embodiment, the operating temperature of the X-ray detector 14 is kept constant by keeping the temperature of the cooling water 5 supplied to the cooling tube 16 constant, thereby the characteristics of detected X-rays can be stabilized.

Further, according to this embodiment, the following advantages can be obtained because the X-ray tube device 1 is cooled by the cooling water 5, which has cooled the X-ray detector 14, through the heat exchanger 4. First, it is preferable to keep the X-ray detector 14 at an approximately room temperature from the view point of stabilizing image quality. In contrast, it is said that the X-ray tube device 1 may be kept at, for example, 75° C. or less. Moreover, the heat value of the X-ray detector 14 is sufficiently smaller than that of the X-ray tube device 1. Accordingly, the X-ray tube device 1 can be sufficiently cooled by the cooling water 5 that has cooled the X-ray detector 14. If the cooling water 5 is circulated reversely, since the temperature of the cooling water is increased (to, for example, 40° C.) by cooling the X-ray tube device 1, it cannot be used to cool the X-ray detector 14.

Further, it is also contemplated to simultaneously supply the cooling water 5 to the X-ray detector 14 and X-ray tube device 1 disposed in parallel with each other through the cooling water tube 18 disposed in parallel with each other. In this case, however, the number of the cooling water tubes 18 passing through the space formed in the interiors of the wiring pole 41, the wiring tube 45, the slider 27, the arm supporting device 23, and the supporting arm 21 is increased to 4 pieces that is twice the two pieces used in this embodiment. In particular, the size of a hole passing through a rotary coupling portion between the arm supporting device 23 and the slider 27 and the size of a hole passing through a movable coupling portion between the arm supporting device 23 and the supporting arm 21 must be increased. According to this embodiment, however, since the number of the cooling water tubes 18 passing through the spaces is the two pieces, it is possible to reduce the sectional area of the space formed in the interior of the supporting arm 21.

Further, according to this embodiment, since water having a large specific heat is used as the heat transfer medium, a cooling efficiency can be improved and the heat transfer medium can be easily handled. However, the heat transfer medium of the present invention is not limited to water, and various fluids capable of transferring heat may be applied.

Next, an example of installation of the cooling tube 16 for the X-ray detector 14 will be explained. The cooling tube 16 for the X-ray detector 14 is composed of a tube which is made of copper or the like and in the interior of which the cooling water 5 flows. The cooling tube 16 can be disposed on a surface of the glass casing 15 in which the X-ray detector 14 is accommodated in a meandering shape. According to this method, the cooling tube 16 can be easily installed eliminating the need of processing the X-ray detector 14 accommodated in the glass casing 15. However, since glass has low heat conductivity of 1.0 to 1.4 (W/m·k), there is a possibility that the cooling efficiency is deteriorated.

Figure 3:
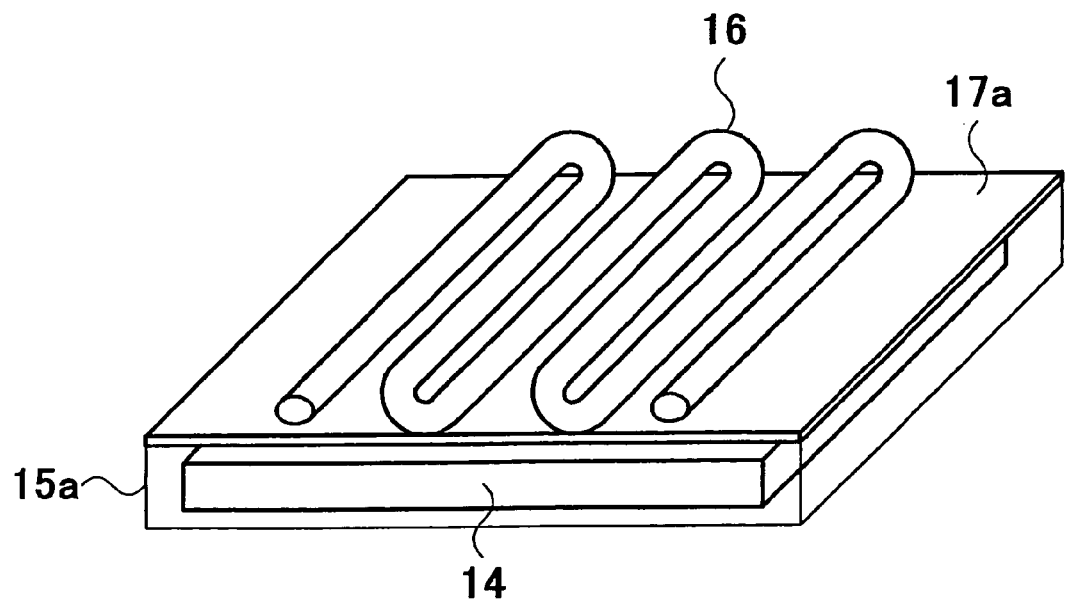
FIG. 3 is an outside view showing an example of installation of a cooling tube according to an embodiment in the X-ray detector of the present invention.

FIG. 3 is an outside view showing an example of installation of a cooling tube of an X-ray detector according to the present invention. In this embodiment, a heat conductive plate 17a such as a copper plate or the like having high heat conductivity is attached to a surface of a glass casing 15a in a meandering shape, and the cooling tube 16 is disposed on the conductive plate 17a in the meandering shape. According to this embodiment, since the heat conductive plate having the high heat conductivity is attached to the surface of the casing in which the X-ray detector is accommodated, a heat absorbing area through which heat is absorbed from the casing is increased, thereby the cooling efficiency can be improved.

Figure 4:
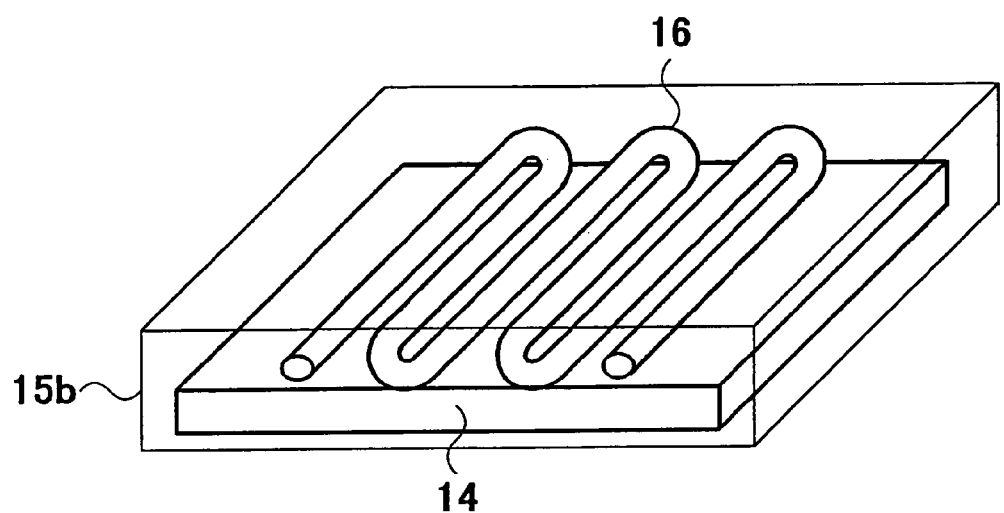
FIG. 4 is an outside view showing an example of installation of a cooling tube according to another embodiment in the X-ray detector of the present invention.

FIG. 4 is an outside view showing an example of installation of a cooling tube of an X-ray detector according to another embodiment of the present invention. In this embodiment, the cooling tube 16 is disposed on a surface of the X-ray detector 14 in the meandering shape in the interior of a glass casing 15b. According to this embodiment, since the X-ray detector can be directly cooled, the cooling efficiency can be improved.

Figure 5:
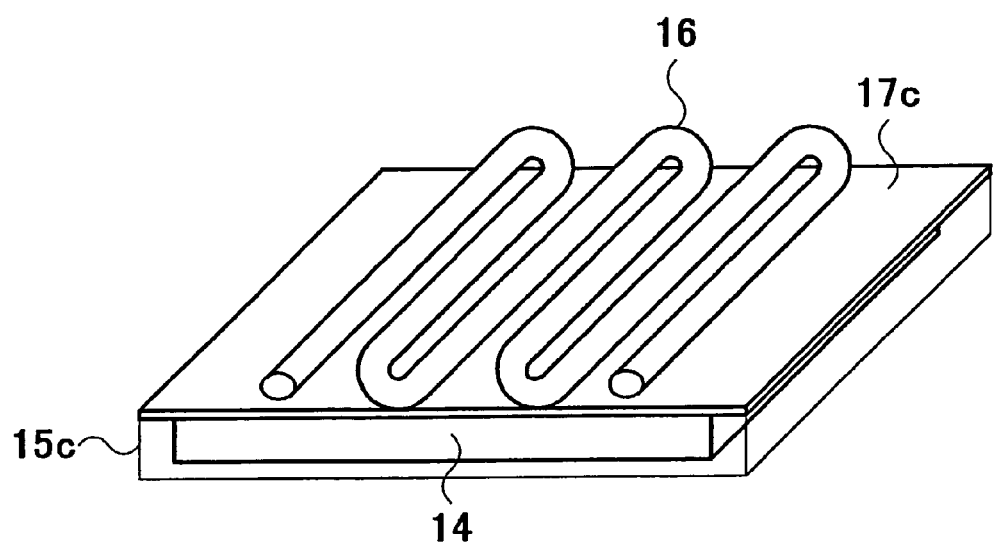
FIG. 5 is an outside view showing an example of installation of a cooling tube according to still another embodiment in the X-ray detector of the present invention.

FIG. 5 is an outside view showing an example of installation of a cooling tube of an X-ray detector according to still another embodiment of the present invention. In this embodiment, the upper surface of a glass casing 15c is composed of a heat conductive plate 17c having high heat conductivity, and the cooling tube 16 is disposed on the heat conductive plate 17c in the meandering shape. When the heat conductive plate 17c is composed of a copper plate, since the copper plate has heat conductivity of about 400 (W/m·k), a heat release value which is about 400 times that of a glass sheet can be obtained. Further, when the heat conductive plate 17c is composed of a member having strength larger than that of glass, the thickness of the heat conductive plate 17c can be reduced and the heat release value can be more increased. When the thickness of the heat conductive plate 17c is set to, for example, one tenth that of a glass plate, the heat release value is increased by 10 times. According to this embodiment, the cooling efficiency can be improved because the heat release value of the casing, in which the X-ray detector is accommodated, is increased.

Although the examples, in which the X-ray detector is accommodated in the glass casing and hermetically sealed therein, have been described in the respective embodiments described above, the present invention is by no means limited thereto, and the casing can be formed using other materials. That is, the casing, in which the X-ray detector is accommodated and hermetically sealed, is preferably formed of materials that have a good X-ray transmitting property and are suitable for hermetically sealing the X-ray detector, and the casing can be formed of, for example, glass, epoxy resin, carbon fiber, and the like.

The invention claimed is:

1. An X-ray diagnosis apparatus comprising:
   an X-ray generator for irradiating X-rays to an object;
   a planer type X-ray detector for detecting the X-rays irradiated from the X-ray generator and passed through the object;
   first circulating means for circulating a first heat transfer medium for absorbing the heat generated in the X-ray generator;
   second circulating means for circulating a second heat transfer medium for absorbing the heat generated in the planer type X-ray detector;
   a heat exchanger for heat-exchanging the heat between the first heat transfer medium circulated by the first circulating means and the second heat transfer medium circulated by the second circulating means; and
   cooling means being coupled to the second circulating means for cooling the second heat transfer medium.

2. An X-ray diagnosis apparatus according to claim 1, characterized in that the heat exchanger transfers the heat of the first heat transfer medium to the second heat transfer medium.

3. An X-ray diagnosis apparatus according to claim 1, further comprising:
   a control means for detecting the temperature of the second heat transfer medium cooled by the cooling means and controlling the cooling means so that the detected temperature is kept within a set range.

4. An X-ray diagnosis apparatus according to claim 1, characterized in that the planer type X-ray detector comprises a plurality of X-ray detecting elements disposed two-dimensionally and flatly and hermetically sealed in a casing, and a cooling tube into which the second heat transfer medium flows is thermally connected to one of the surfaces of the casing on which the X-ray detecting elements are disposed.

5. An X-ray diagnosis apparatus according to claim 4, characterized in that the cooling tube comprises a copper tube disposed on the surface in a meandering shape.

6. An X-ray diagnosis apparatus according to claim 1, characterized in that the planer type X-ray detector comprises:
   a plurality of X-ray detecting elements disposed two-dimensionally and flatly; and
   a casing in which the plurality of X-ray detecting elements are hermetically sealed, wherein
   a heat conductive plate is attached to one of the surfaces of the casing, and a cooling tube, in which the second heat transfer medium flows, is thermally attached to the heat conductive plate.

7. An X-ray diagnosis apparatus according to claim 6, characterized in that the cooling tube is formed of a copper tube meandering on a surface of the heat conductive plate, and the heat conductive plate is formed of a copper plate.

8. An X-ray diagnosis apparatus according to claim 1, characterized in that the planer type X-ray detector comprises:
   a plurality of X-ray detecting elements disposed two-dimensionally and flatly;
   a casing in which the plurality of X-ray detecting elements are accommodated and one of the surfaces of which opens; and
   a heat conductive plate for hermetically sealing the open surface of the casing, wherein
   a cooling tube, in which the second heat transfer medium flows, is thermally attached to the outside surface of the heat conductive plate.

9. An X-ray diagnosis apparatus comprising:
   an X-ray generator;
   a planer type X-ray detector;
   a supporting arm for supporting the X-ray generator and the planer type X-ray detector in confrontation with each other;
   an arm supporting device for supporting the supporting arm;
   a high voltage cable for supplying a high voltage to the X-ray generator; and
   a cooling system for cooling the X-ray generator and the X-ray detector, wherein
   the cooling system comprises:
      first circulating means for circulating an insulating oil for absorbing the heat generated in the X-ray generator;
      second circulating means for circulating a second heat transfer medium comprising water for absorbing the heat generated in the planer type X-ray detector;
      a heat exchanger for heat-exchanging the heat between the insulating oil circulated by the first circulating means and the second heat transfer medium circulated by the second circulating means;
      cooling means being coupled to the second circulating means for cooling the second heat transfer medium;
      temperature detecting means for detecting temperature of the second heat transfer medium flowing out from the cooling means; and
      control means for controlling the cooling means so that the detected temperature of the second heat transfer medium is kept within a set range.

10. An X-ray diagnosis apparatus according to claim 9, characterized in that a second heat transfer medium moving path is formed of a flexible tube, and the tube is inserted into a space formed in interiors of the supporting arm and the arm supporting device and connected to the cooling tube and the heat exchanger.

11. An X-ray diagnosis apparatus according to claim 10, characterized in that the cooling system comprises:
- a vessel in which the second heat transfer medium is stored; and
- a pump for suctioning the second heat transfer medium in the vessel; wherein
- the cooling means cools the second heat transfer medium in the vessel; and
- the second circulating means is formed to flow the second heat transfer medium suctioned from the vessel by the pump in the cooling tube and then to flow the second heat transfer medium in the heat exchanger and to return it to the vessel.

12. An X-ray diagnosis apparatus according to claim 9, characterized in that:
- the second circulating means comprises:
    - a cooling tube thermally coupled with the X-ray detector; and
    - a heat transfer medium moving path for introducing the second heat transfer medium to one end of the cooling tube, introducing the second heat transfer medium discharged from the other end of the cooling tube to an end of a heat transfer medium flow path of the heat exchanger, and returning the second heat transfer medium discharged from the other end of the heat transfer medium flow path of the heat exchanger to the cooling means; and
- the cooling means supplies the second heat transfer medium to the heat exchanger and to the cooling tube.

* * * * *